US005866584A

United States Patent [19]
Cincotta et al.

[11] Patent Number: 5,866,584
[45] Date of Patent: *Feb. 2, 1999

[54] THERAPEUTIC PROCESS FOR THE TREATMENT OF THE PATHOLOGIES OF TYPE II DIABETES

[75] Inventors: Anthony H. Cincotta, Andover, Mass.; Albert H. Meier, Baton Rouge, La.

[73] Assignee: The Board of Supervisors of Louisiana State University and Agricultural and Mechanical College, Baton Rouge, La.

[ * ] Notice: The term of this patent shall not extend beyond the expiration date of Pat. No. 5,468,755.

[21] Appl. No.: 465,818

[22] Filed: Jun. 6, 1995

Related U.S. Application Data

[63] Continuation of Ser. No. 158,153, Nov. 24, 1993, Pat. No. 5,468,755, which is a continuation of Ser. No. 813,153, Dec. 23, 1991, abandoned, which is a continuation-in-part of Ser. No. 463,327, Jan. 10, 1990, abandoned, which is a continuation-in-part of Ser. No. 192,332, May 10, 1988, abandoned.

[51] Int. Cl.$^6$ .................................................. A61K 31/44
[52] U.S. Cl. .......................................... 514/288; 514/866
[58] Field of Search ..................................... 514/288, 866

[56] References Cited

U.S. PATENT DOCUMENTS

| | | |
|---|---|---|
| 3,074,847 | 1/1963 | Bigsby et al. . |
| 3,752,814 | 8/1973 | Fluckier et al. ........................ 544/346 |
| 3,752,888 | 8/1973 | Fluckiger et al. ...................... 514/250 |
| 3,922,347 | 11/1975 | Bach et al. .............................. 514/288 |
| 4,054,660 | 10/1977 | Clemens et al. ........................ 514/288 |
| 4,239,763 | 12/1980 | Milvec et al. ........................... 514/288 |
| 4,659,715 | 4/1987 | Meier et al. ............................. 514/288 |
| 4,749,709 | 6/1988 | Meier et al. ............................. 514/288 |
| 4,783,469 | 11/1988 | Meier et al. ............................. 514/288 |
| 5,006,526 | 4/1991 | Meier et al. ............................. 514/288 |

FOREIGN PATENT DOCUMENTS

| | | |
|---|---|---|
| 890369 | 3/1982 | Belgium . |
| 3722383 | 1/1988 | Germany . |
| 57-8231 | 9/1980 | Japan . |
| 2192541 | 1/1988 | United Kingdom . |
| 2192541 | 2/1988 | United Kingdom . |

OTHER PUBLICATIONS

*Molecular and Cellular Biochemistry*, vol. 67, pp. 19–23, 1985 by Lobato et al.
*Deutschen Gesellschaft fur innere Medizin*, Apr. 25–29, 1976 by Landgraf et al, "Therapie der diabetischen Stoffwechsellage bel Hyperprolactinamien und Akromegaire".
*Postgraduate Medical Journal*, Jan. 1980, vol. 56, pp. 11–14, "Effect of bromocriptine on maturity onset diabetes".
Barnett, *Post Graduate Medical J.* 56:11–14, 1980.
Bartness et al., *J. Exp. Zoology* 244:437–454, 1987.
Berle, *Acta endocr. Suppl. 173*, Abstract No. 104, 1973.
Cassar, J. et al. "Bromocriptine Treatment of Acromegaly," *Metabolism* 26: 539–546 (1977).
Cincotta et al. *J. Endocrinol. 106:* 177–181, 1985.
Cincotta et al. *J. Endocrinol. 106*:173–176, 1985.
Martin et al., *Neuroendocrinology* 52: 9–14, 1990.
Martin et al., *The Condor* 75: 369–374, 1973.
Chemical Abstracts (109 66888W) 1988.
Chemical Abstracts (112 75 773 u) 1990.
Burns et al., *Chronopharmacology and Chronotherapeutics, Int'l Symp. on Chronopharm. and Chronother.*, Florida A&M University, 1988.
Harel et al., *Proc. La. Acad. of Sci.*, 38:125, 1975.
Joseph et al., *Proc. Soc. Exp. Biol. Med.*, 146:1150–1155, 1974.
Komorowski et al., *Aliment. Nutr. Metab.*, 1(4): 293, 1980.
Larsson et al., *Lakartidningen* (Sweden), 82 (50):4425, 1985.
Martin et al., "Hormonal Control of Orientation in the White–Throated Sparrow, Zonatrichia Albicollis." *Chronobiology*, pp. 641–646, 1974.
Martin et al., *Proc. La Acad. of Sci.*, 38:127, 1975.
Martin et al., *Am. Zoologist*, 18(3):572, 1978.
Martin, D., "Hormonal Regulation of Migratory Orientation in the White–Throated Sparrow, Zonatrichia Albicollis." Diss. LSU, 1974.
Martin, D., "Factors Influencing the Circadian Rhythm of Locomotor Activity in the Anabatoid Fish, (1969) *Trichogaster Trichopterus Sumatranus*." Thesis. Sam Houston State College, 1969.
Meier et al., *Experientia*, 48:248–253, 1992.
Meier et al., *Physiol. Zool.*, 41(1):95–103, 1968.
Southern et al., *J. Anim. Sci.*, 68:931–936, 1990.
Cincotta et al. *Life Sciences* 45:2247–2254, 1989.
Cincotta, *J. Endocrinol.* 103:141–146, 1984.
Cincotta et al., *J. Endocrinol.* 120:385–391, 1989.
Cincotta et al. *Ann Nutr Metab* 33:305–314, 1989.
Cincotta et al., *Experientia* 43:416–417, 1987.
Cincotta et al. *Horn Metabol Res* 21:64–68, 1989.
Dolocek, R. et al. "Bromocriptine and glucose tolerance in acromegalics," *Pharmatherapeutica* 3: 100–106 (1982).
Eisemann et al., *J. of Animal Sci.* 59(1)95–104, 1984.

(List continued on next page.)

*Primary Examiner*—Kevin E. Weddington
*Attorney, Agent, or Firm*—Darby & Darby

[57] ABSTRACT

A process for the long term modification and regulation of lipid and carbohydrate metabolism—generally to reduce obesity, insulin resistance, and hyperinsulinemia or hyperglycemia, or both (these are the hallmarks of noninsulin dependent, or Type II diabetes)—by administration (i.e., by oral, sublingual or parenternal administration) to a vertebrate, animal or human, of a dopamine agonist, e.g., bromocriptine. Administration of the bromocriptine is made over a limited period at a time of day dependent on the normal circadian rhythm of insulin resistant and insulin sensitive members of a similar species. Insulin resistance, and hyperinsulinemia and hyperglycemia, or both, can be controlled in humans on a long term basis by such treatment inasmuch as the short term, daily administration resets hormonal timing in the neural centers of the brain to produce long term effects.

25 Claims, No Drawings

OTHER PUBLICATIONS

Eisenmann et al., *J. of Animal Sci.* 59(1)86–94, 1984.

Emata et al., *J. Exp. Zoology* 233:29–34, 1985.

Eskildsen, P.C. et al, "Long–Term Treatment of Acromegaly with Bromocriptine," *Acta Endocr.* 87:687–700 (1978).

Horseman et al., *General and Comparative Endocrinology* 38:269–274, 1979.

Horseman et al., *J. Endocr.* 82:367–372, 1979.

Joseph et al., *J. Exp. Zool.* 178(1):59–62, 1971.

Lee et al., *J. of Exp. Zool.* 166(3):307–316, 1967.

Lobato et al. *Mol. and Cell. Biochem.* 67:19–23, 1985.

Martin et al., *Neuroendocrinology* 52: 9–14, 1990.

Martin et al., *The Condor* 75: 369–374, 1973.

Meier et al., *General and Comparative Endocrinology* Suppl. 3:499–508, 1972.

Meier, *Amer. Scientist* 61(2)184–187, 1973.

Meier et al., *Biology of Reproduction* 8:400–410, 1973.

Meier et al., *Proc. Soc. Exp. Biol. and Med.* 133(4):1113–16, 1970.

Meier et al., *Science* 173:1240–42, 1971.

Meier et al., *Gen. & Comp. Endocrin.* 17:311–318, 1971.

Meier et al., *Proc. Soc. for Exp. Bio. & Med.* 137:408–415, 1971.

Meier et al., *Gen. & Comp. Endocrin.* 8(1):110–114, 1967.

Meier et al., *Transactions of the American Fisheries Society* 113:422–431, 1984.

Meier et al., *Current Ornithology* 2:303–343, 1984.

Meier et al., Circadian hormone basis for seasonal conditions in the gulf killifish Fundulus grandi In *Comparative Endocrinology*, pp. 141–144. Galliard et al. (eds), Elsevier/North Holland Biomedical Press, Amsterdam (1978).

Meier et al., *Amer. Zool.* 16:649–659, 1976.

Meier et al., *Amer. J. of Physiology* 232(2):E193–E196, 1977.

Miller et al., *J. Interdiscpl. Cycle Res.* 14(1):75–84, 1983.

Miller et al., *J. Interdiscipl. Cycle Res.* 14(2):85–94, 1982.

Moore et al., *Biology of Reproduction* 36:47–58, 1987.

Ottenweller et al., *Life Sciences* 28:1033–1040, 1981.

Spieler et al., *Life Sciences* 22:255–258, 1977.

Steinbeck, K. and J.R. Turtle, "Treatment of Acromegaly-with Bromocryptine," *Aust. N.Z. J. Med.* 9: 217–224 (1979).

Thomas et al., *Sem. des Hosp. de Paris.* 53(34–35):1857–1862, 1977.

Wass, J.A.H. et al. "An Assessment of Glucose Intolerance In Acromegaly and Its Response to Medical Treatment," *Clin. Endocr.* 12:53–59 (1980).

Wilson, *Chrono. Bio. Int.* 6:113–121, 1989.

Cassar, J. et al. "Bromocriptine Treatment of Acromegaly," *Metabolism* 26: 539–546 (1977).

Dolocek, R. et al. "Bromocriptine and glucose tolerance in acromegalics," *Pharmatherapeutica* 3: 100–106 (1982).

Eskildsen, P.C. et al. "Long–Term Treatment of Acromegaly with Bromocriptine," *Acta Endocr.* 87: 687–700 (1978).

Steinbeck, K. and J.R. Turtle, "Treatment of Acromegaly-with Bromocryptine," *Aust. N.Z. J. Med.* 9: 217–224 (1979).

Wass, J.A.H. et al. "An Assessment of Glucose Intolerance In Acromegaly and Its Response to Medical Treatment," *Clin. Endocr.* 12:52–59 (1980).

THERAPEUTIC PROCESS FOR THE TREATMENT OF THE PATHOLOGIES OF TYPE II DIABETES

RELATED APPLICATIONS

This is a continuation of application Ser. No. 08/158,153, filed Nov. 24, 1993, now U.S. Pat. No. 5,468,755, which is a continuation of 07/813,135, filed Dec. 23, 1991, now abandoned which is a continuation-in-part of application Ser. No. 07/463,327, filed Jan. 10, 1990 now abandoned, which is a continuation-in-part of Ser. No. 07/192,332 filed May 10, 1988, now abandoned.

1. FIELD OF THE INVENTION

This invention relates to a process for the reduction in vertebrates, animals or humans, of body fat stores, and reduction of insulin resistance, hyperinsulinemia, which is often associated with insulin resistance, and hyperglycemia, or reduction of plasma glucose. In particular, it relates to timed administrations of a dopamine agonist, by oral, sublingual or parenternal administration, to reduce and control over an extended period high insulin resistance which, with obesity and hyperinsulinemia or hyperglycemia, or both, are pathologies characteristic of the onset of noninsulin dependent, or Type II diabetes.

2. BACKGROUND

Diabetes, one of the most insidious of the major diseases, can strike suddenly or lie undiagnosed for years while attacking the blood vessels and nerves. Diabetics, as a group, are far more often afflicted with blindness, heart disease, stroke, kidney diseases hearing loss, gangrene and impotence. One third of all visits to physicians are occasioned by this disease and its complications, and diabetes and its complications are a leading cause of death in this country.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally metabolized in the liver to $CO_2$ and $H_2O$ (50%); to glycogen (5%), and to fat (30–40%), which is stored in fat depots. Fatty acids are circulated, returned to the liver and metabolized to ketone bodies for utilization by the tissues. The fatty acids are also metabolized by other organs, fat formation being a major pathway for carbohydrate utilization. The net effect of insulin is to promote the storage and use of carbohydrates, protein and fat. Insulin deficiency is a common and serious pathologic condition in man. In Type I diabetes the pancreas produces little or no insulin, and insulin must be injected daily for the survival of the diabetic. In Type II diabetes the pancreas produces insulin, but the amount of insulin is insufficient, or less than fully effective due to cellular resistance, or both. In either form there are widespread abnormalities, but the fundamental defects to which the abnormalities can be traced are (1) a reduced entry of glucose into various "peripheral" tissues and (2) an increased liberation of glucose into the circulation from the liver (increased hepatic glucogenesis). There is therefore an extracellular glucose excess and an intracellular glucose deficiency which has been called "starvation in the midst of plenty". There is also a decrease in the entry of amino acids into muscle and an increase in lipolysis. Thus, these result, as a con sequence of the diabetic condition, in elevated levels of glucose in the blood, and prolonged high blood sugar which is indicative of a condition which will cause blood vessel and nerve damage. Obesity, or excess fat deposits, is often associated with increasing cellular resistance to insulin which precedes the onset of frank diabetes. Prior to the onset of diabetes, the pancreas of the obese are taxed to produce additional insulin; but eventually, perhaps over several years, insulin productivity falls and diabetes results.

The reduction of body fat stores on a long term, or permanent basis in domestic animals would obviously be of considerable economic benefit to man, particularly since animals supply a major portion of man's diet; and the animal fat may end up as de novo fat deposits in man. The reduction of body fat stores in man likewise would be of significant benefit, cosmetically and physiologically. Indeed, obesity, and insulin resistance, the latter of which is generally accompanied by hyperinsulinemia or hyperglycemia, or both, are hallmarks of Type II diabetes. Controlled diet and exercise can produce modest results in the reduction of body fat deposits. Unfortunately however no effective treatment has been found until now for controlling either hyperinsulinemia, or insulin resistance. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also found in the setting defined by higher-than-normal levels of insulin—i.e., hyperinsulinemia—when there is present normal or elevated levels of blood glucose. Despite decades of research on these serious health problems, the etiology of obesity and insulin resistance is unknown.

The principal unit of biological time measurement, the circadian or daily rhythm, is present at all levels of organization. Daily rhythms have been reported for many hormones inclusive of the adrenal steroids, e.g., the glucocorticosteroids, notably cortisol, and prolactin, a hormone secreted by the pituitary. In an early article, discussing the state-of-the-art at that time, it is reported that "Athough correlations have been made between hormone rhythms and other rhythms, there is little direct evidence that the time of the daily presence or peaklevel of hormones has important physiological relevance." See *Temporal Synergism of Prolactin and Adrenal Steroids* by Albert H. Meier, General and Comparative Endocrinology, Supplement 3, 1972 Copyright 1972 by Academic Press, Inc. The article then describes avian physiological responses to prolactin injections given over daily periods. These responses include increases and decreases in body fat stores, dependent on the time of day of the injection and season, the season being a determinant of normal high body weight and consequent high fat stores or low body weight and consequent low fat stores within the animal. Prolactin was thus found to stimulate fattening only when injected at certain times of the day, and the time of the response to prolactin was found to differ between lean animals and fat animals. In an article titled *Circadian and Seasonal Variation of Plasma Insulin and Cortisol Concentations in the Syrian Hamster, Mesocricetus Auratus* by Christopher J. de Souza and Albert H. Meier, Chronobiology International, Vol. 4, No. 2, pp 141–151, 1987, there is reported a study of circadian variations of plasma insulin and cortisol concentrations in scotosensitive and scotorefractory Syrian hamsters maintained on short and long periods of daylight to determine possible seasonal changes in their daily rhythms. The baseline concentration of insulin was found to be greater in female than in male scotosensitive hamsters on short daylight periods. These differences it is reported, may account for the observed heavy fat stores in female and low fat stores in male scotosensitive hamsters kept on short daylight periods. The plasma concentrations of both cortisol and insulin varied throughout the day for the groups of animals tested,.but were not equivalent. The circadian variations of cortisol were similar irrespective of sex, seasonal condition and daylight. The circadian variation of insulin, in contrast, differed markedly. Neither the daily feeding pattern or glucose concentration varied appreciably with seasonal condition, or daylight. The time of day, or the season, it is reported do not appear to affect the concentrations in glucose or cortisol levels. It is postulated that the daily rhythms of cortisol and insulin are regulated by different neural pacemaker systems, and that changes in the phase relations of circadian systems account in part for seasonal changes in body fat stores. The circadian rhythms of prolactin and the glucocorticosteroid hormones, e.g., cortisol, have thus been perceived as having important though far from fully understood roles in regulating daily and seasonal changes in body fat stores and in the organization and integration of total animal metabolism. See *Circadian Hormone Rhythms in Lipid Regulation*, by Albert H. Meier and John T. Burns, Amer. Zool. 16:649–659 (1976).

Insulin is a hormone with a multitude of biological activities, many of which are tissue specific. For example, insulin can augment milk production in the mammary gland, stimulate fat synthesis in the liver, promote the transport of glucose into muscle tissue, stimulate growth of connective tissues, and the like. The effects of the insulin molecule in one tissue are not necessarily dependent upon its effect in other tissues. That is, these insulin activities can be and are molecularly separate from each other. In contradistinction from the previous art of Meier and Cincotta which teaches that dopamine agonists (e.g., bromocriptine) inhibit liver cell lipogenic (or fat synthesizing) responsiveness to insulin, the new technology described and demonstrated herein teaches that appropriately timed daily administration of a dopamine agonist (e.g., bromocriptine) has another new and distinctly unique beneficial medicinal capability which is to stimulate whole body (primarily muscle) tissue hypoglycemic (or glucose disposal) responsiveness to insulin. This new discovery of this new medical utility of dopamine agonists (e.g., bromocriptine) represents an entirely opposite effect, upon an entirely different biological activity of the insulin molecule, and upon an entirely different tissue of the body from the previous dopamine agonist work of Meier and Cincotta.

3. OBJECTS

It is the primary objective of the present invention to provide a process, or method, for regulating, and resetting insulin sensitive and plasma glucose and insulin levels of vertebrates, i.e., animals, including humans.

In particular, it is an object to provide a process for resetting the circadian neural centers of animals, including humans, to produce long lasting changes in the amount of body fat stores, the sensitivity of the cellular response of a species to insulin, and overcome hyperinsulinemia and/or hyperglycemia which generally accompanies insulin resistance.

A more specific object is to provide a process for resetting the circadian neural centers of animals, including humans, to decrease obesity and maintain the more normal body fat stores of a lean animal, or lean human, on a long term basis.

A further, and equally specific object is to provide a process for resetting on a long term basis the circadian neural centers, particularly in humans, to increase or improve the sensitivity and responsiveness of the cells to insulin, and suppress hyperinsulinemia and hyperglycemia, or both.

4. THE INVENTION

These objects and others are achieved in accordance with the present invention, characterized as a process, or method, for the regulation of lipid and glucose metabolism to produce long term, lasting, and permanent effects by the administration of timed daily dosages to a vertebrate, animal or human, of a dopamine agonist, or prolactin inhibitor, such as L-dopa and various ergot-related compounds. The dosages are continued on a daily basis for a period sufficient to reset the phase oscillation of the prolactin rhythm, or oscillations of both the prolactin and glucocorticosteroid rhythms which are expressions of the prolactin and glucocorticosteroid neural oscillations, respectively. The phase relationship of the prolactin oscillation, and preferably both neural oscillations are modified and reset such that, on cessation of the daily dosages of the dopamine agonist, or prolactin inhibitor, the lipid metabolism of the animal, or human, continues over a long term period (at least one month), if not permanently, at the altered metabolic setpoint, or setpoints.

A dopamine agonist, or prolactin inhibiting compound is administered to the vertebrate, animal or human, preferably orally, sublingually or by subcutaneous or intramuscular injection into the bloodstream. Thus, a prolactin-inhibiting compound, preferably an ergot-related prolactin-inhibiting compound, is administered to a subject exhibiting any one or more of the symptoms desirable of change, e.g., obesity, insulin resistance, hyperinsulinemia or hyperglycemia. Exemplary of prolactin-inhibiting, ergot related compounds are: 2-bromo-alpha-ergocryptine; 6-methyl-8beta-carbobenzyloxy-aminomethyl-10alpha-ergoline; 1,6-dimethyl-8beta carbobenzyloxy-aminomethyl-10alpha-ergoline; 8-acylaminoergolenes, such as 6-methyl-8alpha-(N-acyl)amino-9-ergolene and 6-methyl-8alpha-(N-phenylacetyl)amino-9-ergolene; ergocornine; 9,10-dihydroergocornine, and D-2-halo-6-alkyl-8-substituted ergolines, e.g., D-2-bromo-6-methyl-8-cyanomethylergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention.

In the treatment of an animal, or human subject, the stores of body fat can be depleted or increased, the treatments continued until the stores of body fat are stabilized at an optimum or near-optimum level dependent on the level of body fat stores desired in the subject, for time sufficient that on termination of the treatment the prolactin rhythm, and preferably both the prolactin and glucocorticosteroid rhythms, is reset to maintain on a long term basis the reduced, or increased, body weight stores. In humans, the objective is almost invariably to reduce body fat stores, and obesity. It has been established that a relationship exists between obesity and insulin resistance, and that obesity can lead to increased insulin resistance. Likewise, it has been established that the circadian rhythms of plasma prolactin and glucocorticosteroid concentrations, respectively, have important consequences in the regulation of body fat stores, and that the phase relationship between the prolactin and glucocorticosteroid levels, respectively, differ in lean and fat animals. In a fat animal prolactin will reach a peak level at a given hour of a 24 hour period (in a human usually near midday), and the prolactin level of a lean animal at another time of day (in a human usually during sleep). In a lean animal the glucocorticosteroids, e.g., cortisol, will peak during a 24 hour period at a given hour (generally at a time different from that of prolactin); in a human generally several hours after waking. Thus, the phase relations of the cortisol and prolactin rhythms differ in lean and fat animals. The peak periods of prolactin and glucocorticosteroid production, respectively, may differ to some extent between male and females of any given species. This being so, it has been found that daily dosages of a dopamine agonist, or prolactin inhibitor, given to an obese subject shortly after the normal time of day that the prolactin is at its peak in a lean subject of the same species and sex will produce a weight reduction in the obese subject. Such treatment will, if continued over a sufficient period, reset on a long term or permanent basis the phase of the neural oscillation for the prolactin rhythm, or the phases of the neural oscillations for both the prolactin and glucocorticosteroid rhythms in the obese individual to that present in a lean subject. The obese subject, on initiation of the treatment with the dopamine agonist, or prolactin inhibitor, will lose body fat stores, and the body fat deposits of the obese subject on continuation of the treatments on a daily basis will drop to and stabilize at that of a lean subject of the same species. On discontinuing the daily treatments, the rise and fall of the prolactin, or prolactin and glucocorticosteroid levels in the blood of the treated patient on a daily basis will correspond to that of a lean subject of the same species, and for a period of long duration. The effect of resetting the prolactin, or prolactin and glucocorticosteroid rhythms, in this manner also increases the sensitivity of the cells of the subject to insulin, reduces hyperinsulinemia or hyperglycemia, or both, and thus alters long term pathologies which are characteristic of the onset of Type II diabetes.

In treating vertebrates, generally, dosages of the dopamine agonist, or prolactin are given once a day on a daily basis, generally over a period ranging from about 10 days to about 150 days, at levels ranging from about 3 micrograms to about 100 micrograms, per pound of body weight, to reset the circadian plasma prolactin rhythm. In treating humans, the dopamine agonist, or prolactin inhibitor, is given daily, preferably at dosage levels ranging from about 3 micrograms to about 40 micrograms, more preferably from 3 micrograms to about 20 micrograms, per pound of body weight. Such treatments over a period of about 10 days to about 1 50 days, preferably about 30 days to about 1 20 days, more preferably from about 30 days to about 90 days, most preferably about 30 days to about 60 days, given an obese person daily just a short period after—generally about 1 hour to about 8 hours thereafter, preferably from about 4 hours to about 8 hours thereafter—the prolactin concentration peaks in a lean person will modify and reset the lipid metabolism of the obese person to that of a lean person. Prolactin peaks in an insulin sensitive lean person during the sleep period, generally at about the middle of the sleep period; and hence the time for administering the dopamine agonist to reduce fat stores in an obese subject, improve the sensitivity of a subject to insulin, suppress hyperinsulinemia, or hyperglycemia, or both suppress hyperinsulinemia and reduce hyperglycemia, ranges from about 1 hour to about 10 hours from the middle of the sleep period, from about 1 hour to about 8 hours—preferably from about 1 hour to about 8 hours from the middle of the sleep period, more perferably from about 1 hour to about 4 hours from the middle of the sleep period. Body fat deposits, inclusive of adipose, arterial wall and plasma fat, within the obese person will be reduced, levelled out and maintained after the treatments are discontinued at that of a lean person, over an extended period of time. A lean or obese person showing the effects of insulin resistance, or hyperinsulinemia and/or hyperglycemia, or both insulin resistance and hyperinsulinemia and/or hyperglycemia, treated with the dopamine agonist, or prolactin inhibitor, will become more sensitive to insulin (i.e., will have a lower insulin resistance), and the effects of hyperinsulinemia and/or hyperglycemia will be reduced on a long term basis. The injections of the dopamine agonist, or prolactin inhibitor, will thus reset the phase relations of the two neural oscillations and their multiple circadian expressions to alter metabolism on a long term basis, if not permanently. In other words, there will be as a result of the timed daily dosages of the dopamine agonist, or prolactin inhibitor, a long term reversal of the major pathologies generally associated with the development of Type II diabetes. The levels of body fat stores, plasma insulin concentrations and insulin resistance, hyperglycemia, or all of these pathologies can be reduced on a long term basis by such or treatments, from the high levels often found in obese, hyperinsulinemic persons to that of the much lower and more desirable levels found in lean insulin sensitive persons.

In terms of the human subject, "obesity can be defined as that body weight over 20 percent above the ideal body weight for a given population" (R. H. Williams, Textbook of Endocrinology, 1974, p. 904–916.). The time of day when the prolactin and glucocorticosteroid levels, respectively, will peak in the blood of humans during a day differs between obese subjects and lean subjects, and the peak in each type of subject can be readily determined by measurement of the fat and lean specimens, as defined. In other animal species what constitutes obese and lean members, respectively, of a species can be readily determined by body weight patterns correlated with the prolactin and glucocorticosteroids levels, respectively, in the plasma of the lean and obese members, respectively. The levels differ between members of the different species, but among members of the same species there is close correlation between the prolactin and glucocorticosterone levels, respectively, at certain time of the day dependent on the obesity or leanness of a given specimen.

These and other features of the invention will be better understood by reference to the following information and data of experimental work with animals and humans. In the examples the terminology "LD" refers to the light/dark cycle, the first number following the expression LD refers to the hours of light, and the second to the hours of darkness in the cycle. Thus LD 14:10 refers to a cycle having 14 hours of light and 10 hours of darkness, and the period of a day is expressed in terms of 2400 hours. The letter n refers to the number of animals in a group, "BW" designates body weight, g represents grams and "$\mu g$" is an expression of micrograms.

In the following example data are given which show the altered phase relationships of the circadian rhythms of plasma corticosteriod and prolactin concentrations in swine; changes beneficial in the treatment of diabetics.

EXAMPLE 1

Adult female pigs, six in number, were given bromocryptine implants (10 mg/pig/day) lasting over a period of time while the pigs were subjected to daily periods of daylight and darkness (12:12). Bromocriptine from implants may be expected to enter the circulation in greater amounts near the onset of daily activity. A control group of six pigs were similarly treated to periods of daylight and darkness except that no bromocryptine was administered to the pigs of the control group. The period of darkness was from 1800 to 0600, and the period of daylight from 0600 to 1800. Daily tests were made of the blood of the pigs at four hour intervals over a 14 day period to determine the plasma cortisol level ($\mu$g/dl) and plasma prolactin level ($\mu$g/ml) of both groups. The average for each series of tests made on each group are given as follows:

| Time | Treated Pigs | Control |
|---|---|---|
| Plasma Cortisol Level ($\mu$g/dl) | | |
| 0800 | 1.9 | 4.8 |
| 1200 | 1.5 | 3.4 |
| 1600 | 3.2 | 1.6 |
| 2000 | 2.8 | 1.9 |
| 2400 | 3.5 | 2.7 |
| 0400 | 3.2 | 5.5 |
| Plasma Prolactin Level ($\mu$g/ml) | | |
| 0800 | 1.8 | 0.5 |
| 1200 | 2.3 | 3.3 |
| 1600 | 2.8 | 1.3 |
| 2000 | 2.4 | 1.2 |
| 2400 | 2.3 | 1.7 |
| 0400 | 1.5 | 0.1 |

The effects of bromocriptine implants on fat stores and plasma concentrations of triglyceride, glucose and insulin are given as follows:

| Treatment | Backfat % control | Triglyceride mg/dl | Glucose mg/dl | Insulin $\mu$V/ml |
|---|---|---|---|---|
| Control | 100 | 52 ± 8 | 99 ± 5 | 10.8 ± 1.8 |
| Bromocriptine | $86^3$ | 27 ± $3^3$ | 86 ± $3^3$ | 8.8 ± 0.3 |

(10 mg/day/pig)

Notes: Backfat thickness was used as an index in determining fat stores. These data were obtained 28 days after treatment of the animals.

Plasma was sampled at 1600, 2000 and 2400 after two weeks of treatment. Each pig of the treatment group and control group was sampled.

These data clearly show that the bromocriptine implants altered the phase relationships of the circadian, rhythms of plasma corticosteriod and prolactin concentrations, and produced changes beneficial to diabetics. The data show that, near sunset, when lipogenesis is normally greatest in pigs, bromocriptine reduced plasma triglyceride concentration by 48%. Since lipid is produced in the liver and transported in the blood to adipose tissue, the triglyceride reduction is further evidence that bromocriptine has an inhibitory effect on fat synthesis and deposition. In addition, although the reduction in plasma insulin concentration was not statistically significant, bromocriptine reduced plasma glucose levels by 13% during the early period of darkness (2000–2400). The reduction in blood glucose, without an increase in blood insulin concentration, can be explained as a decrease in insulin resistance (greater hypoglycemic responsiveness to insulin). Bromocriptine reduced body fat stores by 14% in the 28 day period of treatment.

Further studies were done on humans, these indicating that the symptoms of non insulin dependent, or Type II diabetes can be reduced by treatment with bromocriptine. Examples follow.

EXAMPLE 2

A 50 year old woman, showing the symptoms of diabetes, was daily given bromocriptine tablets (1.25–2.50 mg/day), taken orally, just after awakening. At the beginning of the treatment, blood glucose concentration was shown by routine testing to be near 250 mg/dl. In the weeks following the initial treatment, the patient's glucose levels fell to 180 mg/dl, to 155 mg/dl, to 135 mg/dl, to 97 mg/dl and to 101 mg/dl. Fasting levels below 120 mg/dl are considered normal. Body weight and indices of body fat were also reduced about 12% by the treatment.

EXAMPLE 3

A 45 year old woman was being treated with a hypoglycemic agent (diabenase) which had reduced the blood glucose of the patient from 250 mg/dl to about 180 mg/dl during one year of treatment. Following daily oral administration of bromocriptine (parlodel, 1.25–2.5 mg/day) about an hour after awakening, the blood glucose level fell dramatically to 80 mg/dl in 2 weeks. Removal of the hypoglycemic agent allowed glucose levels to rise and remain near 100 mg/dl (a normal level) in the succeeding two months. Body weight and fat were reduced about 10% by the bromocriptine treatment.

EXAMPLE 4

A 55 year old man weighing nearly 300 pounds was known to be a diabetic but had resisted all previous admonitions for treatment. At the beginning of oral bromocriptine treatment (parlodel, 2.5 mg/day), given between two and three hours after awakening, his plasma glucose concentration averaged near 350 mg/dl. During 2.5 months of bromocriptine treatment, body weight and plasma glucose concentration gradually but continuously decreased. Body weight has dropped 22 pounds and plasma glucose levels decreased to 160 mg/dl.

The following exemplifies the effect of bromocriptine treatments on a group of persons, both male and female, diagnosed as having noninsulin dependent, Type II, diabetes. The individual subjects described by reference to Examples 2, 3 and 4 are included within the subject population included in the Table given in the example.

EXAMPLE 5

Fifteen persons, diagnosed with noninsulin dependent (Type II) diabetes, were treated with bromocriptine to determine the effects of the treatments on body fat and hyperglycemia. Seven diabetics (2 males and 5 females) were being treated orally with stimulants for endogenous insulin secretion (hypoglycemic drugs: diabenase and micronase) and seven diabetics (2 males and 5 females) were receiving daily injections (morning and evening administrations) of insulin. Only those who were found to be very hyperglycemic (i.e., fasting plasma glucose>160 mg/dl) in the morning after a night of fasting and before insulin injection or taking other medications were accepted for the study. One obese man with severe hyperglycemia who refused conventional treatment for diabetes was permitted to participate in this bromocriptine study and is included with the group receiving hypoglycemic drugs.

Bromocriptine was taken orally daily at times calculated to reset circadian hormone rhythms to phase relationships that cause loss of body fat. Generally, bromocriptine was administered in the morning within 5 hours after awakening. Nausea was usually avoided by starting with the lower dosage (1.25 mg) for 2–3 days and then raising the dosage levels to 2.5 mg daily. Only mild nausea was observed by less that 10% of the participants and was transient, lasting only for the first few days. The participants were carefully instructed not to alter their daily activity or eating habits during the course of treatment. Patient compliance was excellent as indicated by weekly interviews of subjects who monitored their food intake, and the transient anorexic effects sometimes produced by higher doses of bromocriptine did not occur in this study.

Skinfold thickness was measured on the left side of the body by a trained anthropometrist in four regions: biceps, triceps, subscapular, and suprailiac, following the recommendations of the International Biological Program. Because of its frequent use, percent body fat was estimated from the common logarithm of the sum of the four skinfolds, using the equations of Durnin and Rahman and of Siri. A recent study indicates very similar estimations of body fat by hydrodensitometry and skinfold thickness measurement methods. Skinfold measurements were taken initially and at weekly intervals by the same individual. Blood pressure was also determined at these times. Morning fasting plasma glucose in the diabetic group was determined initially and after 4–8 weeks.

Reference is made to the Table below.

TABLE

Reductions of Plasma Glucose Concentration and Body Fat in Type II Diabetes after 4–8 Weeks of Timed Bromocriptine Treatment

| Parameter Examined | Subjects on Hypo-glycemic Drugs (8) | | Subjects Receiving Insulin (7) | |
|---|---|---|---|---|
| | Initial | Final | Initial | Final |
| Plasma Glucose (mg/dl) | 231 ± 19 | 166 ± 19[1] | 283 ± 14 | 184 ± 22[1] |
| Plasma Glucose (% initial) | | 72 ± 6[1] | | 65 ± 8[1] |
| Total Body Weight (pounds) | 255 ± 21 | 253 ± 20 | 182 ± 9 | 182 ± 10 |
| Loss of Body Weight (pounds) | | −2.4 ± 2.0 | | −0.4 ± 2.0 |
| Skinfold Measurements (% initial)[2] | | 79[1] | | 84[1] |
| Body Fat (% Body Weight) | 36.5 ± 2.3 | 32.9 ± 2.0[1] | 33.4 ± 2.2 | 31.7 ± 1.7[1] |
| Body Fat Loss (pounds) | | −10.0 ± 2.2[1] | | −3.1 ± 0.9[1] |

[1]Every individual in the groups taking hypoglycemic drugs (8 subjects) or insulin (7 subjects) lost plasma glucose, skinfold thickness and total body fat. The losses are significant ($p < 0.05$).
[2]Initial skinfold measurements (mm) for the subscapular, triceps, biceps, and suprailiac regions were 26 ± 3, 14 ± 2, 9 ± 0 and 19 ± 2 in those taking hypoglycemic drugs and 26 ± 2, 15 ± 2, 12 ± 2 and 19 ± 1 in those taking insulin.

Both blood glucose concentrations and skinfold measurements were reduced in every diabetic subject after 4–8 weeks of bromocriptine treatment, as will be observed by reference to the Table. The initial fasting blood glucose concentrations before morning medications for diabetes were 283±14 mg/dl and 231±19 mg/dl for those taking insulin and hypoglycemic drugs, respectively. After 4–8 weeks, mean glucose concentrations were reduced ($p<0.05$; student's t) to 184±22 mg/dl (insulin) and 166±19 mg/dl (hypoglycemic drugs). Oral hypoglycemic medication was completely discontinued during bromocriptine treatment in three individuals and blood glucose levels remained near normal (<120 mg/dl) for at least two months after bromocriptine treatment was terminated. Doses of hypoglycemic drugs and insulin were reduced in three other subjects during bromocriptine treatment.

Body fat stores were substantially reduced by timed bromocriptine treatment in NIDDM subjects taking hypoglycemic drugs as evidenced by a mean reduction of 21% in the skinfold measurements at the four regions examined. This reduction amounts to a mean loss of 10 pounds for each individual and a decline in total body fat of 10.7% within 4 to 8 weeks. The reductions in skinfold (16%), body fat (3.1 pounds) and % body fat (5.1) were less in those subjects taking insulin. Body weights were perhaps slightly reduced (2.4 pounds per subject, not statistically significant) in subjects taking hypoglycemic drugs and not at all reduced in those taking insulin.

These results demonstrate that bromocriptine treatment can dramatically reduce body fat stores in human subjects. Bromocriptine treatment also substantially reduced hyperglycemia within two months in noninsulin dependent (Type II) diabetics. These results were achieved without changing individual existing diets and exercise regimens.

It is incredible that the reductions in body fat (4.4% of the body weight) achieved: in the present study after 6 weeks without food restriction are equivalent to those obtained utilizing a very low calorie diet (420 kcal/day) for a similar period of time. Amatruda and coworkers, in contrast, reported an 8% reduction of body weight in obese NIDDM subjects of which less than 50% can be assumed to be fat under these conditions. Furthermore, Kanders et al reported an average body weight loss of 2.3 pounds per week in nondiabetic obese females subjected to similar very low calorie diets. This also amounts to a reduction of about one pound of fat per week under these restricted calorie conditions, which is less than the fat loss of 1.4 pounds per week average achieved with bromocriptine treatment in the present study.

The reduction of body fat produced by bromocriptine treatment differs in a significant way from reduction of fat achieved by caloric restriction. With very low calorie diets only about 45% of the weight loss is lipid; the remainder includes protein, carbohydrate and water.

The data show that metabolic states are regulated at least in part by an interaction of circadian neuroendocrine rhythms. This hypothesis proposes that the daily rhythms of cortisol and prolactin are individual expressions of two separate circadian systems and that the daily injections of these hormones can reset the phase relations of these two systems. Thus, in a hamster model it has been found that the 0-hour relation resets the circadian oscillations into a pattern that maintains the lean, insulin sensitive state and the 12-hour relation permits retention of a pattern that maintains the obese, insulin resistant state. Another important addition of the present study is that the effects of timed injections of a dopamine agonist, or prolactin inhibiting compound, are long lasting. Apparently once reset, the phase relation of the two circadian oscillations tends to maintain its altered pattern.

Changes in the phase relations of two circadian neuroendocrine oscillations are evidenced by changes in the phase relations of their circadian expressions. This expectation is fulfilled respecting plasma glucocorticosteroid and prolactin rhythms. In several species examined, the phase relations of the two hormone rhythms differ in lean and fat animals.

The phase relation between the circadian rhythm of plasma insulin concentration and the rhythm of lipogenic responsiveness to insulin is shown to differ in lean and fat animals. Whereas the daily interval of lipogenic responsiveness remains near light onset, the phase of the insulin rhythm varies markedly. The peak concentration of insulin, e.g., occurs near light onset in obese female hamsters held on short day-lengths. That is, the daily peaks of the lipogenic stimulus (i.e., insulin) and the lipogenic response to insulin coincide in fat animals and not in lean animals.

The phase relations of both prolactin and insulin rhythms as well as the rhythms of tissue responses to the hormones are important elements in the regulation of lipogenesis. All of these rhythms, then, would be phase adjusted to regulate lipogenesis. Phase adjustment of these and perhaps other rhythms may also account for insulin resistance.

It is apparent that various modifications and changes can be made without departing the spirit and scope of this invention.

Having described the invention, what is claimed is:

1. A process for the therapeutic modification and regulation of lipid metabolism in an animal, or human subject, which comprises administering to a subject in need of treatment, on a timed daily basis a dopamine agonist in dosage amount and for a period sufficient to reduce plasma triglyceride levels in said animal or human subject.

2. The process of claim 1 wherein after discontinuing treatment with the dopamine agonist the effects of the treatment continue for at least one month.

3. The process of claim 1 wherein the dopamine agonist administered on a timed daily basis to said subject is sufficient to modify or reset both the prolactin and glucocorticosteriod rhythms.

4. The process of claim 1 wherein the timed daily dosages of the dopamine agonist are given daily, once a day, over a period ranging from about 10 days to about 150 days, at levels ranging from about 3 micrograms to about 100 micrograms, per pound of body weight.

5. The process of claim 1 wherein the timed daily dosages of the dopamine agonist are given daily in amount ranging from about 3 micrograms to about 40 micrograms, per pound of body weight, in treating humans, over a period of from about 10 days to about 150 days.

6. The process of claim 5 wherein the dosage is given in amount ranging from about 3 micrograms to about 20 micrograms, per pound of body weight, over a period ranging from about 30 days to about 120 days.

7. The process of claim 5 wherein said subject is a human and the dopamine agonist is given daily at times ranging from about 1 hour to about 8 hours after the time corresponding to that in which the prolactin concentration peaks in a lean insulin sensitive person.

8. The process of claim 1 wherein the dopamine agonist is selected from the group consisting of 6-methyl-8 beta-carbobenzyloxy-aminoethyl-10 alpha-ergoline; 1,6-dimethyl-8 beta-carbobenzyloxy-aminomethyl-10 alpha-ergoline; 8-acylaminoergolenes; ergocornine; 9,10-dihydroergocornine; bromocriptine, and D-2-halo-6-alkyl-8-substituted ergolines.

9. A process for the modification and regulation of lipid metabolism in a human subject in need of treatment which comprises administering to the subject, over a period ranging from about 30 days to about 120 days, at levels ranging from about 3 micrograms to about 40 micrograms, per pound of body weight, daily doses of a dopamine agonist at from about 1 to about 10 hours after the normal time of day that the prolactin level is at its peak-in a lean insulin-sensitive subject of the same species and sex, to produce a change of the neuroendocrine system of the subject to mimic that of the lean subject such that plasma triglyceride levels are reduced in said subject in need of treatment.

10. The process of claim 9 wherein the dopamine agonist is selected from the group consisting of 6-methyl-8 beta-carbobenzyloxy-aminoethyl-10alpha-ergoline; 1,6-dimethyl-8 beta-carbobenzyloxy-aminomethyl- 10 alpha-ergoline; 8-acylaminoergolenes; ergocornine; 9,10-dihydroergocornine; bromocriptine, and D-2-halo-6-alkyl-8-substituted ergolines.

11. In a method for treating a vertebrate exhibiting one or more of obesity, insulin resistance, hyperinsulinemia, glucose intolerance, or hyperglycemia by delivery to said vertebrate of a prolactin inhibitor, the improvement which comprises:

confining the delivery of said prolactin inhibitor to the period during the day proximate to the time of day at which the serum prolactin concentration of a lean, insulin-sensitive vertebrate of the same sex and species is low.

12. A method for treating an animal exhibiting one or more of obesity, insulin resistance, hyperinsulinemia, glucose intolerance, or hyperglycemia, comprising:

administering to said animal a therapeutically effective amount of a prolactin inhibitor in a dosage regimen under which the delivery of said prolactin inhibitor is confined to the period during the day proximate to the time of day at which the serum prolactin concentration of a young, lean, insulin-sensitive animal of the same sex and species is low.

13. A method according to claim 11 in which the delivery of said prolactin inhibitor is confined to from about 4 to about 8 hours after the time of day of said peak concentration.

14. A method according to claim 12 in which the delivery of said prolactin inhibitor is confined to from about 4 to about 8 hours after the time of day of said peak concentration.

15. A method according to claim 13 in which said prolactin inhibitor is bromocriptine.

16. A method according to claim 14 in which said prolactin inhibitor is bromocriptine.

17. A method according to claim 15 wherein said bromocriptine is administered in an amount between about 3 and about 40 micrograms per pound of body weight per day.

18. A method according to claim 16 wherein said bromocriptine is administered in an amount between about 3 and about 40 micrograms per pound of body weight per day.

19. The method of claim 11 wherein said prolactin inhibitor is administered daily for at least 10 days.

20. The method of claim 12 wherein said prolactin inhibitor is administered daily for at least 10 days.

21. The method of claim 11 wherein said vertebrate is a human.

22. The method of claim 12 wherein said vertebrate is a human.

23. The method of claim 19 wherein said animal is a human.

24. The method of claim 20 wherein said animal is a human.

25. A method for modifying or regulating glucose metabolism in an animal or human subject in need of such treatment comprising:

administering to said subject a prolactin inhibiting compound on a timed daily basis in a dosage amount and for a period sufficient to achieve in said subject at least one of the following modifications: decrease in insulin resistance, reduction of hyperinsulinemia, increase in glucose tolerance, and reduction of hyperglycemia, wherein said prolactin inhibitor is administered daily for at least 10 days.

* * * * *